(12) United States Patent
Schalm

(10) Patent No.: US 6,905,677 B1
(45) Date of Patent: Jun. 14, 2005

(54) COMBINED HEPATITIS B TREATMENT

(75) Inventor: Solco Walle Schalm, Rotterdam (NL)

(73) Assignee: Stichting Leveronderzoek, Rotterdam (NL)

( * ) Notice: Subject to any disclaimer, the term of this patent is extended or adjusted under 35 U.S.C. 154(b) by 755 days.

(21) Appl. No.: 09/689,637

(22) Filed: Oct. 13, 2000

Related U.S. Application Data

(60) Provisional application No. 60/159,101, filed on Oct. 13, 1999.

(51) Int. Cl.$^7$ .............................................. A61K 31/70
(52) U.S. Cl. ..................... 424/85.7; 424/227.1; 514/43; 514/885; 514/894; 530/351
(58) Field of Search .............................. 424/85.7, 227.1; 514/43, 885, 894, 86, 92, 143, 266; 530/351; 536/26.7

(56) References Cited

PUBLICATIONS

Nicoll et al., Journal of Gastroenterology and Hepatology, (Dec. 1997) 12(12) 843–54.*

* cited by examiner

*Primary Examiner*—Laurie Scheiner
(74) *Attorney, Agent, or Firm*—Finnegan, Henderson, Farabow, Garrett & Dunner, LLP

(57) ABSTRACT

The invention relates to a method of treating patients infected with hepatitis B virus comprising the adminstration of both a nucleoside analogue and interferon-α over a prolonged period of time.

10 Claims, 3 Drawing Sheets

Figure 1

| Weeks | -4 | -2 | 0 | 4 | 8 | 12 | 16 | 20 | 24 | 28 | 32 | 36 | 40 | 44 | 48 | 52 | 56 | 60 | 64 | 68 | 72 | 76 | 78 |
|---|---|---|---|---|---|---|---|---|---|---|---|---|---|---|---|---|---|---|---|---|---|---|---|
| Visit | x | x | x | x | x | x | x | x | x | x | x | x | x | x | x | x | x | x | x | x | x | x | x |
| lab A | x | x | x | x | x | x | x | x | x | x | x | x | x | x | x | x | x | x | x | x | x | x | x |
| lab B | x | x | x | x | x | x | x | x | x | x | x | x | x | x | x | x | x | x | x | x | x | x | x |
| lab C | x | x | x | | | | | | | | | | | | | | | | | | | | x |
| YMDD analysis | | | | | | | x | | | | x | | | | | x | | | | | | | x |
| pregnancy test | x | x | x | x | x | x | x | x | x | x | x | x | x | x | x | x | | | | | | | |
| biopsy | x | | | | | | | | | | | | | | | | | | | | | | (x) |
| med | | | x | x | x | x | x | x | x | x | x | x | x | x | x | x | | | | | | | |

Figure 2

| lab A | lab B | lab C |
|---|---|---|
| Hb, WBC+ differentiation, PT* | AST, ALT | HBV DNA*** |
| platelet count | GGT, alkaline phospatase | HBeAg |
| | total bilirubin | anti-HBe |
| | albumin, creatinine* | HBsAg |
| | **Na, K, ureum, uric acid, LDH | ****anti-HIV, anti-HDV, |
| | amylase, CPK, lactate, total protein | anti-HCV |

\* only at screening, baseline and visit week 0, 16, 32, 52, 64 and 78
\*\* additional laboratory tests: only at screenings visit
\*\*\* in geq/ml
\*\*\*\* additional laboratory tests: only if not done in the past

COMBINED HEPATITIS B TREATMENT

This application claims priority to U.S. Provisional Application No. 60/159,101, filed on Oct. 13, 1999, the contents of which are incorporated herein by reference.

The invention relates to the treatment of humans infected with hepatitis B virus (HBV).

HBV is a small DNA containing virus which infects humans. It is a member of the class of closely related viruses known as the hepadnaviruses, each member of which selectively infects either mammalian or avian hosts, such as the woodchuck and the duck. Recent insights into the mechanism of replication of an RNA intermediate suggest that the reverse transcriptase is a logical chemotherapeutic target. HBV is a viral pathogen of major world-wide importance. The virus is etiologically associated with primary hepatocellular carcinoma and is thought to cause 80% of the world's liver cancer. Clinical effects of infection with HBV range from fever, malaise, nausea, anorexia, abdominal and joint pains to jaundice. Replication of the virus is usually controlled by the immune response, with a course of recovery lasting weeks or months in humans, but infection may be evoking less immunoreactivity leading to persistent chronic liver disease.

In practice, there are two main approaches for treating chronic HBV. One is based on the use of human interferon, in particular interferon-α; the other is based on the use of a nucleoside analogue, such as lamivudine.

Interferon-α is one of the three types of interferon that have been characterized. These three types were originally known as leukocyte, fibroblast and immune interferon, but are nowadays designated interferons α, β, γ, respectively. Interferons form a large family of proteins and are widely distributed in the animal kingdom. Generally, they are species specific. Human interferon-α can be produced by different cell types and HPLC has resolved this type of interferon into over 30 subtypes, each coded by a different gene. Commercially, human interferon-α is manufactured by stimulating the Namalwa human lymphoblastoid cell line with Sendai virus to produce a natural mixture of at least 21 subtypes of interferon-α, which are then purified by chromatography to a purity of 95% and a specific activity of about $100 \times 10^6$ IU/mg protein. Such a product, identified as human interferon α-Nl, is commercially available. It is also possible to prepare human interferon-a using recombinant DNA technology.

Since the early 1980s, advances in production techniques led to the use of both natural and recombinant human interferon-α for the treatment of chronic HBV. Nowadays, interferon-α is generally accepted as the standard agent for treatment of chronic HBV infection. Although this treatment can be regarded as successful in many cases, response rates to treatment with human interferon-α, as judged by sustained loss of viral markers, are generally considered to be less than 50%. For an extensive review of the use of interferons in the treatment of hepatitis, reference is made to the book "Interferons in the Treatment of Chronic Virus Infection of the Liver" by Eddleston and Dixon, Pennine Press, 1990.

Nucleoside analogues form a new generation of drugs used in the treatment of hepatitis B virus. They have been found to show strong in vitro activity and low toxicity. There are three main nucleoside analogues, designated lamivudine, adefovir and entecavir. They all act on the reverse transcriptase enzyme of the hepatitis B virus, but on different priming sites. Lamivudine has been tested in phase III trials.

Adefovir, or [9-(2-phosphonylmethoxyethyl)adenine], or its orally available prodrug adefovir dipivoxil (the [bis (pivaloyloxymethyl)ester prodrug] is inter alia described in Antimicrob. Agents Chemother., 1998, 42(7), 1620–8, and Hepatology 1999, 29(6), 1863–9. The drug is currently under investigation in phase III trials for its anti-HIV activity.

Lamivudine, or (2R,cis)-4-amino-1-(2-hydroxymethyl-1,3-oxathiolan-5-yl-(1H)-pyrimidin-2-one, and its use in the treatment and prophylaxis of viral infections has been disclosed in U.S. Pat. No. 5,047,407. Lamivudine has proven antiviral activity against HIV and other viruses such as HBV. It is commercially available under the trade name Epivir® and Zeffix®. Lamivudine can effectively suppress replication of HBV. However, prolonged lamivudine treatment is hampered by the emergence of drug resistant mutant strains, reported in 14–50% of patients at 1–2 years of treatment. After withdrawal of lamivudine, HBV DNA and hepatic inflammation may return to pre-treatment levels within 1–3 months.

At the $49^{th}$ Annual Meeting of the American Association for the Study of Liver Diseases, Chicago, Nov. 9, 1998 (abstract 901 in Hepatology 1998; 28; 4), the results of a trial were presented, in which trial a combination therapy of 26 weeks of lamivudine and 16 weeks of interferon-α was compared with a conventional lamivudine therapy. This trial was conducted in 238 patients in 63 clinical centers with chronic HBV who previously failed interferon therapy. It was concluded that the combination therapy did not appear promising. The difference in response rate between patients treated with the combination of lamivudine and interferon-α, and patients treated with a placebo was negligible.

The present invention seeks to provide an improved treatment of patients infected with HBV. As outlined above, the conventional treatments all have disadvantages and/or a too low response rate. It is desired to have a treatment which is successful in patients which have previously failed such a conventional treatment. It is further desired to provide a treatment of patients infected with HBV, which treatment has a high response rate even without pre-treatment with one or more of the conventional treatments.

Surprisingly, it has now been found that a very intense response (HBV DNA undetectable by PCR, loss of HBeAg and HBsAg) can be achieved in patients infected with HBV, particularly chronic HBV, by a combined treatment, using both a nucleoside analogue and interferon-α, in a specific protocol of administration. The invention thus relates to a method of treating a human patient infected with hepatitis B virus, wherein during a period of at least 26 weeks a nucleoside analogue and interferon-α are both administered to said patient.

By administering both a nucleoside analogue and interferon-α in the specific protocol according to the present treatment, it has been found possible to achieve significantly better results than with the conventional treatments involving only one of a nucleoside analogue and interferon-α. Moreover, the present treatment has been found to be successful in a number of cases wherein conventional treatment involving only one of said agents did not provoke a response.

The type of nucleoside analogue may be chosen from the group of lamuvidine, adefovir and entecavir. This includes of course prodrugs of all nucleoside analogues, such as adefovir dipivoxil. Particularly good responses have been found using lamivudine. The nucleoside analogue may be administered in the form of any pharmaceutical formulation which can conventionally be used. Examples of possible formulations of lamivudine can be found in WO-A-98/42321. Preferably, the nucleoside analogue is administered in the form of an oral dosage form. For an overview of different nucleoside analogues, reference is made to inter alia Clin. Phamacokinet. 1999, 36(2), 127–43, Antimicrob. Agents Chemoter. 1998, 42(12), 3200–17.

The dose wherein lamivudine is administered is preferably chosen between 50 and 150 mg per day for the period wherein the combined treatment is carried out. Adefovir may be administered in a dose of between 5 and 30 mg per day, whereas entecavir can be administered in a dose of between 0.01 and 1 mg per day.

The subtype of interferon-α used in accordance with the invention is not critical. It is envisaged that the interferon-α may be in any suitable form or formulation. In a preferred embodiment, pegylated interferon-α (PEG-IFN) is used. This form of interferon-α, which is known to the person skilled in the art, can be administered less often and has less adverse effects than standard interferon-α. PEG-IFN need only be administered once or twice a week, whereas of standard interferon-α three injections per week are necessary.

The dose wherein interferon-α is administered is preferably chosen between 30 megaUnits (equivalence for PEG-IFN 100 μg) and 15 megaUnits (equivalence for PEG-IFN 50 μg) per week for the period wherein the combined treatment is carried out. It is preferred that the dose of interferon-α is decreased during treatment, particularly in case of debilitating adverse effects. Preferably, the first part of the period wherein both agents are administered, a higher dose is used than in the second part. In this embodiment, in the first part of the period the dose is preferably 30 megaUnits per week and in the latter period preferably 15 megaUnits per week.

An important aspect of the invention is that during a period of at least 26 weeks both agents are administered to a patient. Preferably, this period is at least 30 weeks. During this period, the agents may be administered at intervals ranging from daily to weekly. It is preferred that the nucleoside analogue is administered daily, while interferon-α is preferably administered once a week. The period wherein both agents are administered will usually not be longer than 52 weeks, as it has been found that longer periods of treatment may be poorly tolerated.

In accordance with the invention it is possible that the period wherein the combined treatment is carried out is preceded or followed by a period wherein only one of the two agents is administered.

BRIEF DESCRIPTION OF THE DRAWINGS

FIGS. 1 and 2 describe the frequency and substance of patient monitoring during a treatment according to the invention.

Figure 3:
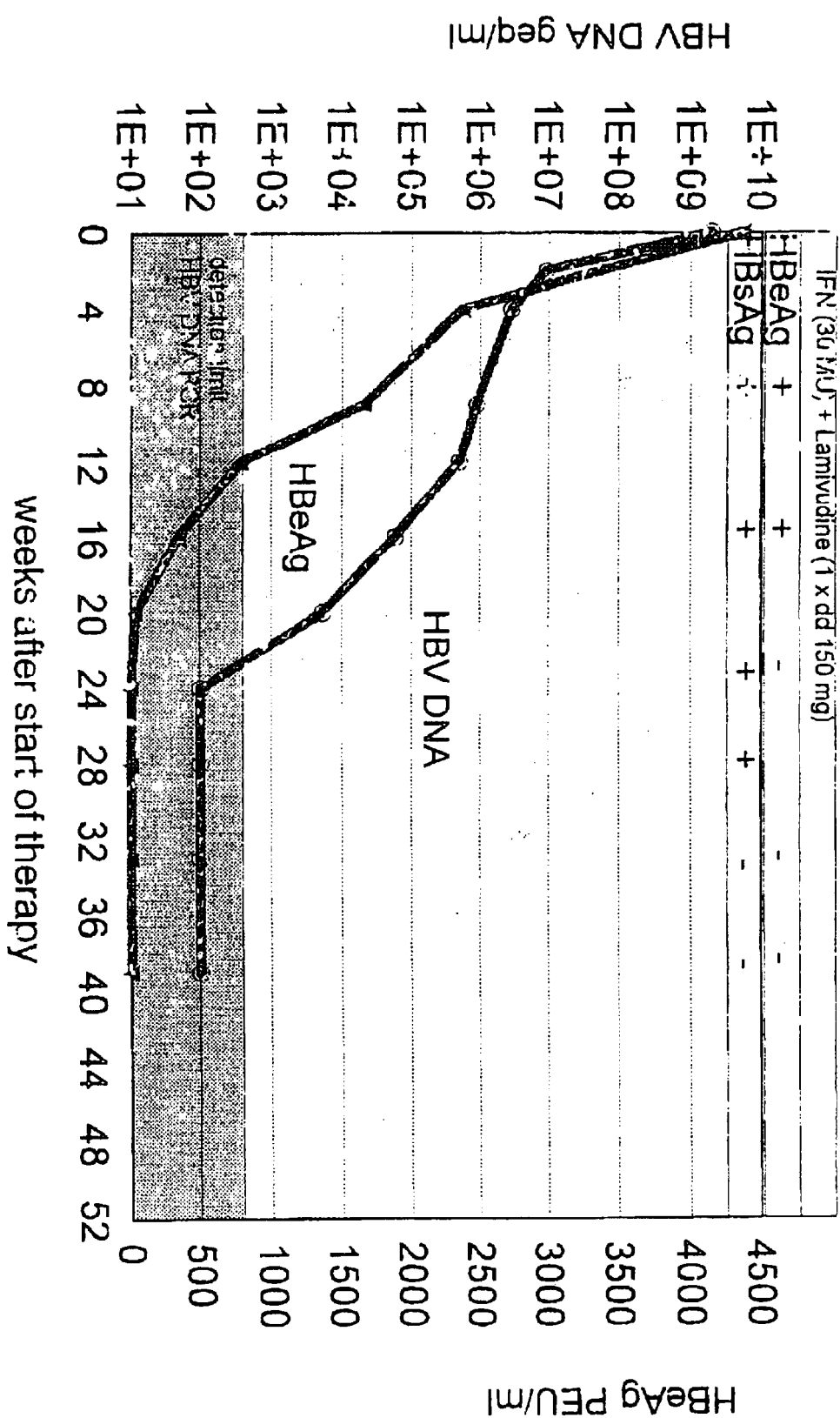
FIG. 3 describes the results of a treatment according to the invention for a 23 year old woman having a known HBV infection for 1 year.

The invention will now be elucidated by the following, non-restrictive examples.

EXAMPLES

Aim

To enhance the efficacy of antiviral therapy to achieve viral clearance (HBeAg negativity) in chronic hepatitis B patients by giving 52 weeks combination therapy of lamivudine and interferon-α (IFN).

Design

All patients will receive lamivudine 150 mg per day in combination with IFN 30 megaUnits (Mu) per week. After 32 weeks IFN will be reduced to 15 MU per week. Therapy will be given for a total treatment period of 52 weeks.

A liver biopsy, taken within 6 months before start of therapy and at the end of follow-up is optional.

| Weeks | 0 | 8 | 16 | 24 | 32 | 40 | 48 | 52 | 68 | 78 |
|---|---|---|---|---|---|---|---|---|---|---|
| IFN | | IFN 30 MU/wk | | | | IFN 15 MU/wk | | | Follow-up | |
| Lamivudine | | Lamivudine 1 × dd 150 mg | | | | | | | | |

Potential Candidates

Potential candidates for treatment are all patients older than 18 years, with a chronic compensated HBV infection (HBsAg positive, HBV DNA positive by hybridization assay) and ALT>2×ULN. These patients will be given an information sheet/consent form.

Screening Potential Candidates (-4 Weeks)

Collect eligibility data: history, physical examination, lab hematology, chemistry and virology, pregnancy test.

Check inclusion criteria: informed consent, ALT>2×ULN, ≧18 yrs, anticonception.

Check exclusion criteria: evidence of other viral, alcoholic drug, hereditary or auto-immune hepatitis, decompensated liver disease, other significant medical illness or condition, pregnancy or contra-indication for interferon therapy.

Baseline Visit (-2 Weeks)

Discuss decision about starting therapy.

Monitoring

In accordance with the schemes shown in FIGS. 1 and 2. Quantitative hepatitis B virus DNA assessment (HBV DNA) was performed by Hybrid Capture assay I (Digene, Murex, detector limit $1.5*10^6$ Eurohep genome equivalent per ml) and if negative, by quantitative PCR (PCRQ, Roche Amplicar, detection limit $10^3$ Eurohep genome equivalent per ml). (See also J. Viral Hepatitis, 1998, 5, 307–312 on limiting dilution polymerase chain reaction in chronic hepatitis B patients, and Hepatology 1999 30, 238–43 on HBeAg and HBsAg in accordance with interferon-α for chronic Hepatitis B infection, the contents of which are incorporated herein by reference). FIG. 3 shows the results (HBV DNA and HBeAg) for a 23 year old woman having a known HBV infection since 1 year.

What is claimed is:

1. A method of treating a human patient infected with hepatitis B virus, which comprises administering to the patient both a nucleoside analogue and interferon-α during a period of at least 26 weeks.

2. A method according to claim 1, wherein the nucleoside analogue and interferon-α a are administered at intervals ranging from daily to weekly.

3. A method according to claim 1, wherein the nucleoside analogue and interferonα are both administered during a period of at least 30 weeks.

4. A method according to claim 1, wherein the period is preceded by a period wherein one of a nucleoside analogue and interferon-α is administered.

5. A method according to claim 1, wherein the period is followed by a period wherein one of a nucleoside analogue and interferon-α is administered.

6. A method according to claim 1, wherein the nucleoside analogue is lamivudine, adefovir or entecavir.

7. A method according to claim 1, wherein during the period lamivudine as the nudeoside analogue is administered in a dose from 50 to 150 mg per day.

8. A method according to claim 1, wherein during the period interferon-α is administered in a dose from 30 megaUnits to 15 megaUnits per week.

9. A kit of parts, comprising at least a first container and a second container, wherein the first container comprises a nucleoside analogue and the second container comprises interferon-α.

10. A kit of parts according to claim 9, wherein the nucleoside analogue is lamivudine, adefovir, or entecavir.

* * * * *

UNITED STATES PATENT AND TRADEMARK OFFICE
CERTIFICATE OF CORRECTION

PATENT NO. : 6,905,677 B1
DATED : June 14, 2005
INVENTOR(S) : Solco Walle Schalm It is certified that error appears in the above-identified patent and that said Letters Patent is hereby corrected as shown below:

<u>Title page,</u>
Item [57], ABSTRACT,
Line 2, "adminstration" should read -- administration --.

<u>Column 4,</u>
Line 57, "interferon-α a are" should read -- interferon-α are --.
Line 60, "interferonα" should read -- interferon-α --.

<u>Column 5,</u>
Line 3, "clalm" should read -- claim --.
Line 4, "nudeoside" should read -- nucleoside --.

Signed and Sealed this

Thirtieth Day of August, 2005

JON W. DUDAS
*Director of the United States Patent and Trademark Office*